United States Patent [19]

Wright et al.

[11] 4,108,862
[45] Aug. 22, 1978

[54] 3-(4-CHROMANYLAMINO)-2-OXAZOLIDI-NONES

[75] Inventors: George C. Wright; Marvin M. Goldenberg, both of Norwich, N.Y.

[73] Assignee: Morton-Norwich Products, Inc., Norwich, N.Y.

[21] Appl. No.: 812,124

[22] Filed: Jul. 1, 1977

[51] Int. Cl.$^2$ ............................................ C07D 263/26
[52] U.S. Cl. ................................ 260/307 C; 424/272
[58] Field of Search .................................. 260/307 C

[56] References Cited
PUBLICATIONS

Elliott et al., C.A. 77, 56400n (1972).

*Primary Examiner*—Raymond V. Rush
*Attorney, Agent, or Firm*—Anthony J. Franze

[57] ABSTRACT

Certain 3-(4-chromanylamino)-2-oxazolidinones are useful as gastric antisecretory agents.

2 Claims, No Drawings

3-(4-CHROMANYLAMINO)-2-OXAZOLIDINONES

This invention is concerned with chemical compounds and particularly with compounds of the formula:

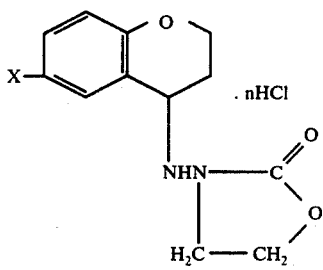

wherein X is hydrogen or amino and $n$ is 0 or 1.

The compounds of this invention possess pharmacological activity. For example, upon peroral administration to rats at a dose of about 100 mg/kg about one hour prior to pylorus ligation of the rat's stomach, inhibition of gastric acid output and reduction of gastric secretions are elicited.

The compounds of this invention can be readily composed in various pharmaceutical dosage forms such as elixirs, capsules, tablets, suspensions and the like using commonly employed carriers and excipients with which there is no incompatibility.

In order that this invention may be readily available to those skilled in the art, the following examples illustrate currently preferred methods of making it.

EXAMPLE I

A. 3-[(4-Chromanylidene)amino]-2-oxazolidinone

A 62 g (0.61 mole) portion of 3-amino-2-oxazolidinone was charged in a 500 ml, 3-necked flask equipped with a thermometer, stirrer and reflux condenser, and treated successively with 92 ml of $H_2O$, 8 ml of 10% HCl and 42 g (0.28 mole) of 4-chromanone in 200 ml of ethanol. The reaction mixture was refluxed for 36 hrs., stripped in vacuo to one-half volume and cooled in the refrigerator overnight. The slurry was filtered and the white crystalline solid washed with 50 ml of isopropanol then 200 ml of ether and dried; m.p. 105°–108°. Yield: 44 g (68%).

The filtrate was extracted with 250 ml of $CHCl_3$, and the $CHCl_3$ extract dried over $MgSO_4$, filtered and stripped in vacuo. The residue was slurried in 100 ml of ether, allowed to stand 3 hrs., filtered, and the product dried; m.p. 50°–62°. Yield: 9 g (14%). Then the combined crude products were recrystallized from 350 ml of isopropanol, washed with 40 ml of isopropanol, 150 ml of ether and dried; m.p. 111°–113°.

Yield: 40 g (62%).

Anal. Calcd. for $C_{12}H_{12}N_2O_3$: C, 62.06; H, 5.21; N, 12.06. Found: C, 62.02; H, 5.24; N, 12.06.

B. 3-(4-Chromanylamino)-2-oxazolidinone Tetartohydrate

A 75 g (0.32 mole) portion of A. and 750 ml of methanol were placed in a 2-l, high pressure bottle, with 9 g of 5% $Pd/BaSO_4$, and subjected to hydrogenation at 40 psig. The hydrogen uptake was 21 lb. (theory: 22 lb. at 27°). The reduction mixture was heated to reflux, filtered, cooled overnight in the refrigerator, and again filtered. The resultant white crystalline solid was washed with 100 ml of cold methanol, ether, and dried; m.p. 104°–105°. Yield: 69 g (90%).

The product was recrystallized from 400 ml of methanol, washed with 100 ml of cold methanol, ether, and dried; m.p. 105°–107°. Yield: 63 g (82%).

Anal. Calcd. for $C_{12}H_{14}N_2O_3.\frac{1}{4}H_2O$: C, 60.36; H, 6.12; N, 11.73. Found: C, 60.70; H, 6.28; N, 11.74.

EXAMPLE II

A. 3-[(6-Nitro-4-chromanylidene)amino]-2-oxazolidoxone

An 85 g (0.44 mole) portion of 6-nitro-4-chromanone in 460 ml of benzene was treated with 1 ml of HCl (isopropanol) solution, using mechanical stirring, and refluxed until all water was removed via a Dean-Stark trap. The dried solution was treated with 46 g (0.46 mole) of 3-amino-2-oxazolidinone and refluxed for 2.6 hrs. A 7.9 ml portion of water was collected (theory: 7.9 ml). The reaction mixture was filtered hot, cooled to 10°–11° for 3 hrs. and filtered. The orange crystalline solid was washed with 100 ml of benzene, ether and dried; m.p. 168°–170°. Yield: 107 g (88%).

The product was recrystallized from 650 ml of nitromethane (Darco), washed with 100 ml of cold nitromethane, ether and dried; m.p. 170°–171°.

Yield: 84 g (69%).

Anal. Calcd. for $C_{12}H_{11}N_3O_5$: C, 51.99; H, 4.00; N, 15.16. Found: C, 51.96; H, 4.03; N, 15.14.

B. 3-[(6-Amino-4-chromanyl)amino]-2-oxazolidinone Hydrochloride

A 37 g (0.13 mole) portion of A., 400 ml of isopropanol, and 8 g of 5% Pd/C (50% moisture) were placed in a 1.8 l. pressure bottle and subjected to hydrogenation at 50 psig. The hydrogen uptake was 38 lbs. (theory: 36 lbs. at 26°) in 22 hrs. The reduction mixture was warmed, adding an additional 500 ml of isopropanol Darco, and filtered. The filtrate was adjusted to pH 2 with 30 ml of HCl (isopropanol) solution, refrigerated overnight, and filtered. The cream colored crystalline solid was washed with 100 ml of isopropanol, ether, and dried; m.p. 212°–214° dec. Yield: 32 g (82%).

A 30 g portion of the product was recrystallized from 500 ml of methanol (Darco) and washed with 50 ml of methanol ether, and dried; m.p. 212°–213° dec. Yield: 21 g (58%).

Anal. Calcd. for $C_{12}H_{15}N_3O_3.HCl$: C, 50.44; H, 5.64; N, 14.71. Found: C, 50.61; H, 5.71; N, 14.94.

What is claimed is:

1. The compound 3-(4-chromanylamino)-2-oxazolidinone tetartohydrate.

2. The compound 3-[(6-amino-4-chromanyl)amino]-2-oxazolidinone hydrochloride.

* * * * *